(12) United States Patent
Erb et al.

(10) Patent No.: US 9,513,443 B2
(45) Date of Patent: Dec. 6, 2016

(54) OPTICAL FIBER-FINE WIRE CONDUCTOR AND CONNECTORS

(71) Applicants: John Lawrence Erb, Plymouth, MN (US); Stephen Sundquist, Minnetonka, MN (US); James Edward Shapland, Vadnais Heights, MN (US); Robert Glenmore Walsh, Newport, OR (US); Jin Shimada, Grantsburg, WI (US)

(72) Inventors: John Lawrence Erb, Plymouth, MN (US); Stephen Sundquist, Minnetonka, MN (US); James Edward Shapland, Vadnais Heights, MN (US); Robert Glenmore Walsh, Newport, OR (US); Jin Shimada, Grantsburg, WI (US)

(*) Notice: Subject to any disclaimer, the term of this patent is extended or adjusted under 35 U.S.C. 154(b) by 0 days.

(21) Appl. No.: 14/331,200

(22) Filed: Jul. 14, 2014

(65) Prior Publication Data
US 2014/0318825 A1    Oct. 30, 2014

Related U.S. Application Data

(63) Continuation-in-part of application No. 14/165,559, filed on Jan. 27, 2014, which is a continuation of application No. 12/806,743, filed on Aug. 18, 2010, now abandoned, application No. 14/331,200, which is a continuation-in-part of application No. 14/029,439, filed on Sep. 17, 2013, which is a continuation of application No. 12/590,851, filed on Nov. 12, 2009, now abandoned, which is a continuation-in-part of application No. 12/156,129, filed on May 28, 2008, now abandoned, application No. 14/331,200, which is a continuation-in-part of application No. 14/184,580, filed on Feb. 19, 2014, which is a continuation-in-part of application No. 12/804,271, filed on Jul. 16, 2010, now Pat. No. 8,692,117, application No. 14/331,200, which is a continuation-in-part of application No. 13/831,001, filed on Mar. 14, 2013, now Pat. No.
(Continued)

(51) Int. Cl.
*A61N 1/05* (2006.01)
*G02B 6/38* (2006.01)
*G02B 6/44* (2006.01)

(52) U.S. Cl.
CPC ............... *G02B 6/3817* (2013.01); *A61N 1/05* (2013.01); *G02B 6/4416* (2013.01)

(58) Field of Classification Search
CPC .......... A61N 1/05; A61N 1/056; A61N 1/057; A61N 1/0504
See application file for complete search history.

(56) References Cited

U.S. PATENT DOCUMENTS 3,980,806 A    9/1976    May
4,276,144 A    6/1981    Hahn
(Continued)

*Primary Examiner* — George Evanisko
(74) *Attorney, Agent, or Firm* — John M. Berns

(57) ABSTRACT

A small diameter, shielded, fine wire glass fiber conductor which is capable of transmitting optical and electrical signals in environments with electromagnetic interference or radio frequency interferences. The conductor includes a fiber core, a first insulation layer, a conductive layer, a second insulation layer, a shielding layer, and an outer coating. Applications include use in aerospace, automotive, and other vehicles as well as potential use in electrostimulation devices, such as pacemaker leads, vascular guidewires and other medical applications.

15 Claims, 15 Drawing Sheets

Related U.S. Application Data 9,242,100, and a continuation-in-part of application No. 13/831,100, filed on Mar. 14, 2013, now abandoned, and a continuation-in-part of application No. 13/849,229, filed on Mar. 22, 2013, now Pat. No. 9,025,598, and a continuation-in-part of application No. 13/849,334, filed on Mar. 22, 2013, now Pat. No. 9,193,313.

(56) References Cited

U.S. PATENT DOCUMENTS

| | | |
|---|---|---|
| 4,407,561 A | 10/1983 | Wysocki |
| 4,408,604 A | 10/1983 | Hirshorn et al. |
| 4,418,984 A | 12/1983 | Wysocki et al. |
| 4,575,187 A | 3/1986 | Howard et al. |
| 4,701,575 A | 10/1987 | Gupta et al. |
| 4,785,815 A | 11/1988 | Cohen |
| 4,798,206 A | 1/1989 | Maddison et al. |
| 4,873,989 A | 10/1989 | Einzig |
| 4,896,209 A | 1/1990 | Matsuzaki |
| 4,911,712 A | 3/1990 | Harrington |
| 5,117,828 A | 6/1992 | Metzger et al. |
| 5,218,171 A | 6/1993 | Aldissi |
| 5,433,744 A | 7/1995 | Breyen et al. |
| 5,463,138 A | 10/1995 | Muller |
| 5,500,012 A | 3/1996 | Brucker et al. |
| 5,531,779 A | 7/1996 | Dahl et al. |
| 5,593,430 A | 1/1997 | Renger |
| 5,750,930 A | 5/1998 | Buck et al. |
| 6,104,961 A | 8/2000 | Conger et al. |
| 6,129,685 A | 10/2000 | Howard |
| 6,167,314 A | 12/2000 | Fischer et al. |
| 6,178,356 B1 | 1/2001 | Chastain et al. |
| 6,195,411 B1 | 2/2001 | Dinsmore |
| 6,319,188 B1 | 11/2001 | Lovoi |
| 6,356,791 B1 | 3/2002 | Westlund et al. |
| 6,366,819 B1 | 4/2002 | Stokes |
| 6,428,537 B1 | 8/2002 | Swanson et al. |
| 6,456,888 B1 | 9/2002 | Skinner et al. |
| 6,564,107 B1 | 5/2003 | Bodner et al. |
| 6,697,676 B2 | 2/2004 | Dahl et al. |
| 6,711,443 B2 | 3/2004 | Osypka |
| 6,792,316 B2 | 9/2004 | Sass |
| 6,849,074 B2 | 2/2005 | Chen et al. |
| 6,879,861 B2 | 4/2005 | Benz et al. |
| 6,930,242 B1 | 8/2005 | Helfer et al. |
| 7,010,356 B2 * | 3/2006 | Jog ............... A61N 1/0551 600/373 |
| 7,077,837 B2 | 7/2006 | Sahagian |
| 7,079,902 B2 | 7/2006 | Soukup et al. |
| 7,137,395 B2 | 11/2006 | Fried et al. |
| 7,231,260 B2 | 6/2007 | Wallace et al. |
| 7,420,124 B2 | 9/2008 | Michael et al. |
| 7,447,533 B1 | 11/2008 | Fang et al. |
| 7,519,432 B2 | 4/2009 | Bolea et al. |
| 7,865,044 B2 * | 1/2011 | Farhadiroushan ....... G01J 5/08 385/12 |
| 7,883,536 B1 | 2/2011 | Bendett et al. |
| 7,917,213 B2 | 3/2011 | Bulkes et al. |
| 8,000,808 B2 | 8/2011 | Hegland et al. |
| 8,380,277 B2 * | 2/2013 | Atalar ................ A61N 1/05 600/374 |
| 2001/0055904 A1 | 12/2001 | Sawada et al. |
| 2002/0052636 A1 | 5/2002 | Bardy et al. |
| 2002/0183818 A1 | 12/2002 | Williams et al. |
| 2002/0189845 A1 | 12/2002 | Gorrell |
| 2003/0013958 A1 | 1/2003 | Govari et al. |
| 2003/0077935 A1 | 4/2003 | Stein et al. |
| 2003/0083724 A1 | 5/2003 | Jog et al. |
| 2003/0195602 A1 | 10/2003 | Boling |
| 2003/0195603 A1 * | 10/2003 | Scheiner ............ A61N 1/056 607/122 |
| 2004/0024440 A1 | 2/2004 | Cole |
| 2004/0064174 A1 | 4/2004 | Belden |
| 2004/0122499 A1 | 6/2004 | Westlund |
| 2004/0193021 A1 | 9/2004 | Zdeblick et al. |
| 2004/0243210 A1 | 12/2004 | Morgan et al. |
| 2004/0254483 A1 | 12/2004 | Zdeblick et al. |
| 2005/0090885 A1 | 4/2005 | Harris et al. |
| 2005/0096720 A1 | 5/2005 | Sharma et al. |
| 2005/0103932 A1 | 5/2005 | Huynh |
| 2006/0009830 A1 | 1/2006 | Atkinson et al. |
| 2006/0095105 A1 | 5/2006 | Jog et al. |
| 2006/0106443 A1 | 5/2006 | Michael et al. |
| 2006/0247702 A1 | 11/2006 | Stegemann et al. |
| 2006/0293741 A1 | 12/2006 | Johnson et al. |
| 2007/0038052 A1 | 2/2007 | Swoyer et al. |
| 2007/0067000 A1 | 3/2007 | Strother et al. |
| 2007/0088208 A1 * | 4/2007 | Yasuzawa ......... A61B 5/04001 600/345 |
| 2007/0088417 A1 | 4/2007 | Schouenborg |
| 2007/0288077 A1 | 12/2007 | Bulkes et al. |
| 2007/0293923 A1 | 12/2007 | Soltis et al. |
| 2008/0015625 A1 | 1/2008 | Ventura et al. |
| 2008/0039916 A1 | 2/2008 | Colliou et al. |
| 2008/0077220 A1 | 3/2008 | Reddy |
| 2008/0097567 A1 | 4/2008 | Haldeman |
| 2008/0183257 A1 | 7/2008 | Imran et al. |
| 2008/0188910 A1 | 8/2008 | Spaide |
| 2008/0217587 A1 | 9/2008 | Gaudiana et al. |
| 2008/0255629 A1 | 10/2008 | Jenson et al. |
| 2009/0204193 A1 | 8/2009 | Kokones et al. |
| 2009/0299446 A1 * | 12/2009 | Lovoi ................ A61N 1/0551 607/119 |
| 2010/0057179 A1 | 3/2010 | Storey |
| 2010/0114271 A1 * | 5/2010 | Sommer ............. A61B 5/0006 607/115 |
| 2010/0182023 A1 | 7/2010 | Pena et al. |
| 2010/0183269 A1 | 7/2010 | Mahapatra et al. |
| 2010/0278491 A1 | 11/2010 | Noddings |
| 2011/0116751 A1 | 5/2011 | Terlizzi et al. |
| 2011/0121922 A1 | 5/2011 | Blair et al. |
| 2011/0220408 A1 | 9/2011 | Walsh et al. |
| 2011/0245714 A1 | 10/2011 | Volckaerts |
| 2011/0272192 A1 | 11/2011 | Walsh et al. |
| 2011/0301657 A1 | 12/2011 | Walsh et al. |
| 2012/0277600 A1 | 11/2012 | Greenhut |
| 2013/0041447 A1 | 2/2013 | Erb et al. |
| 2013/0266280 A1 * | 10/2013 | Sakabe ................ H01B 11/22 385/101 |

\* cited by examiner

OPTICAL FIBER-FINE WIRE CONDUCTOR AND CONNECTORS

CROSS REFERENCE TO RELATED APPLICATIONS

This application claims benefit of priority to each of the following applications. This application claims benefit of priority as a Continuation-in-Part of U.S. patent application Ser. No. 14/165,559, filed Jan. 27, 2014, which is a Continuation of U.S. patent application Ser. No. 12/806,743, filed Aug. 18, 2009. This application also claims benefit of priority as a Continuation-in-part of U.S. patent application Ser. No. 14/029,439 filed Sep. 17, 2013, which is a Continuation of U.S. patent application Ser. No. 12/590,851, filed Nov. 12, 2009, which is a Continuation-in-part of U.S. patent application Ser. No. 12/156,129, filed May 28, 2008. This application further claims the benefit of priority as a Continuation-in-part of U.S. application Ser. No. 14/184,580 filed Feb. 19, 2014 which is a Continuation of U.S. Pat. No. 8,692,117, filed Jul. 16, 2010 issued Apr. 8, 2014. This application further claims the benefit of priority as a Continuation-in-part of U.S. application Ser. No. 13/831,001, filed Mar. 14, 2013, Ser. No. 13/849,229, filed Mar. 22, 2013, Ser. No. 13/831,100 filed Mar. 14, 2013, and Ser. No. 13/849,334, filed Mar. 22, 2013. All of the above applications are incorporated herein by reference in their entirety.

BACKGROUND OF THE INVENTION

Reliable and rapid data communication is important in terrain and aerospace vehicles to ensure accurate reporting of various vehicle conditions. For instance, in order to properly and safely operate an aircraft, a pilot (or remote operator) is typically provided with updates on the operational status of the personnel, passengers, physical integrity, or mechanical moving parts of the aircraft. Numerous update types are possible; these are but a few of the many types of tangible and operational data points that can be important.

Communication can be difficult in these vehicles because of harsh environmental conditions and difficulty in routing communication channels. In addition, there is a tradeoff between the desire to monitor data points and the resulting increased vehicle weight and space requirements. The cabling necessary to monitor and transmit data from the far reaches of the vehicle to the operator adds weight and bulk to the vehicle. The more data monitored the more weight and bulk, which reduces the vehicle's performance and increases its fuel consumption. In addition, as the data may result in operational changes that must be transmitted back to the data source (or a related area), two way communication is often necessary, further increasing cabling.

These and other matters have presented challenges to communication circuitry and channels for a variety of applications.

As one example, electrical signals maybe interrupted by electromagnetic interference (EMI) or radio frequency interference (RFI). EMI and RFI present challenges to communication circuits and channels. This problem is exacerbated by the plurality of cables in modern vehicles.

EMI is a disturbance that affects an electrical circuit due to electromagnetic induction or electromagnetic radiation from an external source. The effect of the disturbance can range from completely blocking the electrical signal to limiting or degrading the signal. The source of EMI may be either natural such as solar flares from the sun or meteor showers in the atmosphere, or artificial such as localized magnetic fields, adjacent electrical circuits or conductors, power transmission lines, or radio signals. Narrowband EMI is intended radiation from transmissions such as radio or television systems, or cell phones. Broadband EMI is unintentional radiation from sources such as electric power transmission lines. RFI is EMI at high (radio) frequency.

Susceptibility is a measure of how badly a piece of equipment is affected in the presence of EMI. Electromagnetic Pulses (EMP) occur when the disturbance is of short duration or a series of short duration pulses. Examples of this are electrostatic discharge, nuclear electromagnetic pulse, or pulse trains from gasoline ignition systems.

There are four basic coupling mechanisms for EMI. They include conductive, capacitive, magnetic or inductive, and radiated. Conductive coupling happens through direct contact like through a transmission line and can be common-mode (noise in same phase on both conductors) or differential-mode (noise is out of phase on both conductors). Capacitive coupling occurs when a varying electric field exists between two adjacent conductors typically less than a wavelength apart, inducing a change in voltage across the gap. Magnetic or inductive coupling occurs when a varying magnetic field exists between two parallel conductors typically less than a wavelength apart, inducing a change in voltage along the receiving conductor. Radiated or electromagnetic coupling occurs when there is a large distance between a transmitter and a receiver (more than a wavelength) and the transmitter radiates an electromagnetic wave which is picked up by the receiver.

In looking for solutions to EMI, the problem must be characterized into understanding the source and signal creating the interference, the coupling path to the receiver, and the electrical nature of the receiver and the significance of the interference to the function of the receiver. EMI cannot always be completely eliminated, but can be reduced to an acceptable level of interference with a given probability.

Radio reception may be affected by EMI. Analog circuits are particularly affected by EMI. Digital circuits are more immune to noise as they can use error correction techniques to eliminate some or all unwanted EMI interference.

The common methods of reducing electromagnetic interference in devices and metal cored electrical conductor cables have several issues. All require extra components which add size, weight and complexity to the conductors and overall system.

SUMMARY OF THE INVENTION

The inventors have introduced cabling where the conductors incorporate a high strength glass fiber core that may be used for optical transmission of energy or signals, with at least one thin conductive metal layer for conducting electrical current and separated from other conductive layers by an appropriate thickness of insulator. The invention encompasses a wire conductor(s) and optical fiber(s) which can independently transmit electrical and/or optical signals or energy. The inventors also introduce shielding techniques to shield these small diameter conductors from EMI and RFI. Thus, it is the object of the present invention to provide a small diameter, shielded, fine wire glass fiber conductor which is capable of transmitting optical and electrical signals in environments with electromagnetic interference or radio frequency interferences. Such applications include use in aerospace, automotive, and other vehicles as well as potential use in electrostimulation devices, such as pacemaker leads, vascular guidewires and other medical applications.

It is also an object of the present invention to provide for connectors for use with an optical fiber, fine wine conductor. In one embodiment the apparatus includes a fine wire conductor with an outer diameter no greater than about 750 microns, or in another embodiment, 300 microns. The conductor includes a fiber core comprising silica or glass, a first insulative layer on the fiber core, a coaxial first conductive coating on the first insulative layer configured and arranged to carry electrical signals along the length of the conductor, a second insulative layer on the first conductive coating, a shielding layer outside the second insulative layer, and an outer insulating layer.

The apparatus may also have a coating layer between the fiber core and the first insulative layer. The coating layer may be a graphite layer. The apparatus may further include a second conductive coating on the second insulative layer and a third insulative layer on the second conductive coating.

In another embodiment, the apparatus includes a second fine wire conductor. The second fine wire conductor and the first fine wire conductor may be both inside the same shielding layer, or may each have their own shielding layers. The respective shielding layers may be electrically connected. The first and second fine wire conductors can be arranged as a twisted pair in one embodiment.

In another embodiment the first conductive layer includes a first electrically isolated pathway and a second electrically isolated pathway.

In another embodiment, the inventors teach a fine wire conductor and a connector. The connector includes a connector shielding layer adapted to connect to the conductor shielding layer, and a ground connection connected to the connector shielding layer to ground the connector shielding layer to a ground. The connector shielding layer can include a choke filter. The first conductive layer on the conductor can be electrically connected to a first connector conductive layer. Likewise, the conductor's fiber core can be optically linked to an optical mechanism in the connector.

In one embodiment, the drawn fiber core includes a cladding comprised of glass or silica. The cladding, the coating layer or the first insulative layer can hermetically seal the fiber core. In another embodiment the first conductive coating is selected from the group consisting of aluminum, silver, gold, copper or platinum. That coating may be between 200 nm thick and 40 microns thick.

In another embodiment the fine wire conductor is connected to the connector via a contact adhesive. The connector may include a retaining mechanism.

To connect the electrical conductor, metal layer deposited on the glass fiber, with other conductors or devices, a connector must be used to make such connections simple and reliable. The connector must be able to make direct contact between the metal layer on the glass fiber and a second conductive surface(s) without damaging the metal layer or glass substrate. Connectors used with standard metal conductors such as copper or other metal wires use crimps, welding or other techniques that would damage the glass fiber and/or metal layer in the embodied fine wine conductor. Therefore there is a need for a connector that will make direct and durable contact with other conductive surfaces without damaging the fine wire conductor. In some conditions, there is a need to have a connector for both electrical and optical signal transmission.

In another embodiment the invention encompasses connectors that can make electrical contact between the fine wine conductor and other electrical conductors without damaging the glass fiber or metal layer coating. The insulation is removed from the terminal end of the fine wire conductor to expose the metal layer deposited on the glass fiber, thus exposing the conductive surface. If multiple metal layers are used, each can be exposed for making electrical contact. A contact element provides contact with the metal surface on the fiber body without creating areas of high contact stress which could damage the glass fiber or metal layer.

In one embodiment a wire spring, ribbon or ball contact element is used as an electrical contact element with the conductor within the connector assembly. As the fine wine conductor body is inserted into the internal chamber of the connector assembly, the conductive metal layer on the conductor body makes contact with the contact element. The contact element is designed to place a specific tension on the metal layer of the conductor, enough to make reliable contact but not so much as to damage the metal layer or glass fiber. The embodiment could be used with multiple metal layers, with an insulation layer between the metal layers, by using multiple contact elements to contact each metal layer on the conductor body. If there are multiple discrete conductive pathways in a single metal layer, multiple contact elements can be arranged to make electrical contact with each individual, discrete pathway. In this embodiment, the multiple contact elements could be arranged longitudinally or circumferentially around the internal chamber of the connector assembly. Contact elements could be additionally sealed and secured with a conductive adhesive to minimize any movement of the contact element on the thin metal trace on the optical fiber. Adhesive could be applied in similar fashion to insert injection molding or over over-molding with an appropriately designed connector housing to allow for high pressure injection of conduction adhesive In another embodiment, the connector assembly includes one or more spring coils lining the internal chamber (cylindrical tube). The glass fiber with exposed metal layer is inserted into the internal chamber of the connector box with the surrounding coils contacting the metal layer. The coils provide electrical contact while being compressible to maintain the desired contact pressure.

In other embodiments, the electrical contact element(s) of the connector assembly would be conductive elastomeric O-ring(s) between the conductive metal surface on the glass fiber and the connector assembly's conductive pathway. In this embodiment, multiple conductive layers (multi-layers of metal) would use multiple O-ring contact elements arranged longitudinally along the internal chamber of the connector assembly.

In another embodiment, the fine wire conductor with the metal layer exposed is inserted into the internal chamber of the connector assembly. Once positioned, a conductive strap is tightened around the metal layered portion of the fine wire conductor body. The strap would be tightened by rotation of a screw mechanism. The strap would provide uniform electrical contact with the metal layer and secure the fine wine conductor in the connector assembly.

In another embodiment, the fine wire conductor body is held in the connector assembly using a locking cap secured to the outer surface of the conductor body to a retaining mechanism fixed to the connector assembly. The conductor body is inserted into the internal chamber of the connector assembly and the exposed metal layer on the conductor body is mated into a conductive cavity in the connector assembly. The locking cap on the conductor body is then secured to the retaining mechanism on the connector assembly to secure the fine wine conductor in place. There is no need for further securing within the connector assembly. The securing mechanism between the fine wire conductor body and the connector assembly could include a compressible ring to seal the connector assembly. For all embodiments, various sealing mechanisms could be added to the connector assembly or as part of the fine wire conductor body.

Other embodiments would combine the electrical connectors described above with connectors for transmission of optical signal or energy through the glass fiber core.

DETAILED DESCRIPTION OF THE INVENTION

The embodiments described herein include a small diameter, shielded, fine wire glass fiber conductor which is capable of transmitting optical and electrical signals in environments with electromagnetic interference or radio frequency interference, as well as connectors for use with a small diameter fine wire glass fiber conductor. The electrical conductor used to fabricate the conductor is formed from a drawn silica, glass, or sapphire crystalline quartz fiber core, herein referred to collectively as a glass fiber, with at least one conductive metal layer on the core. The glass fiber may be optically conductive. The outer diameter of the fine wire conductor is preferably less than about 750 microns, and may be 200 microns or even as small as 50 microns. Its applications include use in aerospace, automotive, and other vehicles as well as potential use in electrostimulation devices, such as pacemaker leads, vascular guidewires and other medical applications.

Figure 1:
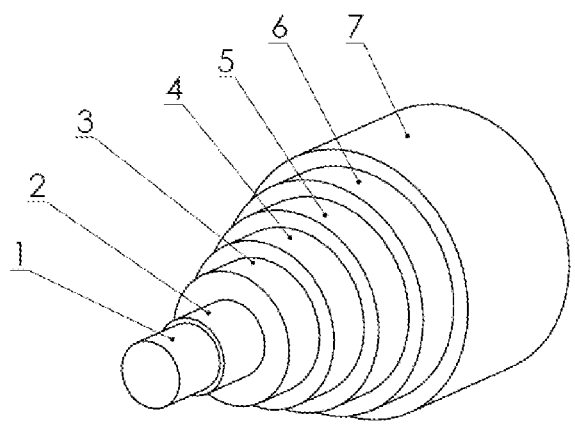
FIG. 1 is an isometric view of a coaxial, multi-conductive-coated-layer glass fiber with nonconductive/electrically insulating layers.

FIG. 1 shows the general construction of a coaxial, multi-conductive-coated-layer glass/silica fiber ("glass fiber") with nonconductive/electrically insulating layers under, between, and over the conductive coated layers. A glass fiber core 1 may be coated with a coating layer 2. The coating layer 2 may be a polymer layer, a sealant, or a thin graphite coating. Additionally, ceramics, and inorganic/organic hybrid materials may be used to seal the silica optical fiber. These hybrid materials could contain silica and enhance bonding to the silica fiber. The coating layer 2 may provide a hermetic or other seal in some embodiments to protect the glass fiber 1 from environmental elements. For example, atmospheric moisture can attack the glass/silica surface and introduce fine cracking, reducing or destroying the strength and durability of the glass fiber core 1.

First insulation layer 3 is then added to coating layer 2. In some embodiments coating layer 2 is not utilized, and first insulation layer 3 is added directly to glass fiber core 1. The insulation layer 3 may be acrylic, polyimide, PTFE, ETFE, FEP, or Parylene. Likewise, the insulation layer 3 could be PVDF or another melt processable fluoro polymer, or an inorganic/organic hybrid material. A PVDF/silica hybrid material created with a sol gel process and applied in a continuous we coating process is one example of a suitable insulation layer 3.

The insulation layer 3 is covered with a first conductive coating 4, which may be made of a highly conductive material such as copper, silver, gold, or platinum. Metals employed in the first conductive coating 4 can also be or include aluminum, titanium, tantalum, or others, as well as metal alloys of which MP35N, a nickel-cobalt based alloy is one example. In one example, a molten metal film, such as gold or silver is applied to the drawn silica, glass, or sapphire crystalline quartz fiber core immediately upon drawing and providing a protective hermetic seal over the silica, glass, or sapphire crystalline quartz fiber, forming a coaxial fine wire optical fiber. In another embodiment, the molten metal film is applied over insulation layers.

Likewise, the first conductive coating 4 can be applied in a Physical vapor deposition process (PVD), for example an aluminum coating can be so applied. In another embodiment the first conductive coating 4 comprises polyoxometalate anions in a conductive base such as a conductive polymer. The polyoxometalate anions comprise anions having the formula $[X_xM_yQ_wO_z]^{q-}$ wherein M and Q are transition metals; X is selected from P, Si, B, Ge, As, or Sb; x, y, w, and z are integers wherein y and z are at least 5 and x and w are at least 0; and q is an integer that represents the charge of the anion. Polyoxometalate anions can have improved capacitance, polarization, electrochemical performance, or stability (or any combination of these improvements) when compared to similar implantable electrodes without the polyoxometalate anions. The polyoxometalate anions may also significantly increase the number of surface sites for electrode materials or coatings First conductive coating 4 can be applied in a coaxial manner. It may also be applied in a patterned manner. For example, first conductive coating 4 can be patterned to produce multiple discrete conductive paths on the same metal layer. These conductive paths may be electrically isolated or may be in parallel for redundancy. The first conductive coating 4 may be deposited using a vapor deposition process (such as evaporative vapor deposition, sputtering, hypersonic cluster beam deposition or other type) to coat the insulation layer. This conductive coating may be thickened using an additional plating process and a similar material. For example, an initial layer could be applied via PVD, with a wet chem plating process used to build the layer thickness. Alternatively, an Aerosol jet process could be utilized to apply additional layers of conductive materials.

In one embodiment, the first conductive coating 4 is applied via a supersonic cluster beam deposition (SCBD) process where nanoparticles are generated using laser or sputtering techniques and then particles are accelerated to supersonic speeds using high pressure gasses or through ultra-high vacuum systems. Nanoparticles traveling at supersonic speeds have enough momentum to embed themselves in polymers and create metalized surfaces after sufficient particle deposition. The advantage of SCBD over other methods includes a mixing of conductive metals and polymer which results in significantly higher adhesion and, ultimately, metalized, metal oxides, carbon nanotube containing surfaces which can be used for enhanced biocompatibility, flexible conductive electrodes and robust coatings In some embodiments first insulative layer 3 is not utilized, and first conductive coating 4 is added directly to glass fiber core 1 or coating layer 2.

A second insulation layer 5 is then applied over the first conductive layer 4. The second insulation layer 5 may comprise a material like or different from the first conductive layer and be optimized for the thickness requirements of an embodiment using a co-extrusion, vapor deposition, or other type of process.

In some embodiments, a second conductive layer 6 is applied over the second insulation layer 5 typically using a similar type of process to the first conductive layer. This may be of a similar metal as the first conductor, or a different material may be chosen because of its effectiveness for a particular application or for use as an EMI shield. Such a material might be copper because of its effectiveness in block radio frequency interference (RFI).

A third insulation layer 7 is applied in a manner detailed above and may be of a similar or different material. As one option to this construction, the first or second conductive layers 4, 6 may be divided into several conductors by masking or etching longitudinal gaps between sections of the layer. Another option to the construction would be to have either conductive layer cut into a spiral pattern. This would also allow multiple conductors and offers benefits for EMI protection in the shielding layer.

Other embodiments provide multiple discrete conductors that can be incorporated into a small diameter wire. Each discrete conductor would typically be electrically isolated from other conductors. Such discrete conductive pathways would allow the delivery of different electrical signals or energy at approximately the same time, thus defined as simultaneous delivery or transmission. The production of multiple discrete conductors can be accomplished by modifying the metal cladding along the length of the conductor. Masking may be pre-applied to the carbon and/or polymer surface to enable a patterned coating of metal on the carbon and/or polymer surface. Such a pattern may be useful for creating two or more separate electrically conductive paths along the length of the fine wire conductor, thus enabling fabrication of a single, dual or multiple electrical conductors upon a single fine wire conductor. The metal can be selectively removed by laser or other technique to produce multiple conductive paths along the length of the conductor. Each independent electrical conductor can be attached to separate electrodes and/or sensors using independent radial attachment strips.

While typically the multiple conductors are electrically isolated, in other instances they may be in parallel for redundancy. If one conductor fails, breaks due to fatigue or injury, or the like, the other will continue to function.

The pattern of the conductive pathways can be applied in specific pattern to accomplish other desired effects, such as applying it in a spiral pattern to provide shielding to reduce potential for electromagnetic interference. One of the discrete conductors could be connected to a ground to shield the other conductive pathways. An additional insulation layer could be applied over the multiple discrete conductive layers with another conductive layer applied to insulation layer to provide additional shielding. Such designs could be used for aerospace applications, to provide light weight, durable, flexible multiple conductors for transmission of electrical and optical signals.

Figure 2:
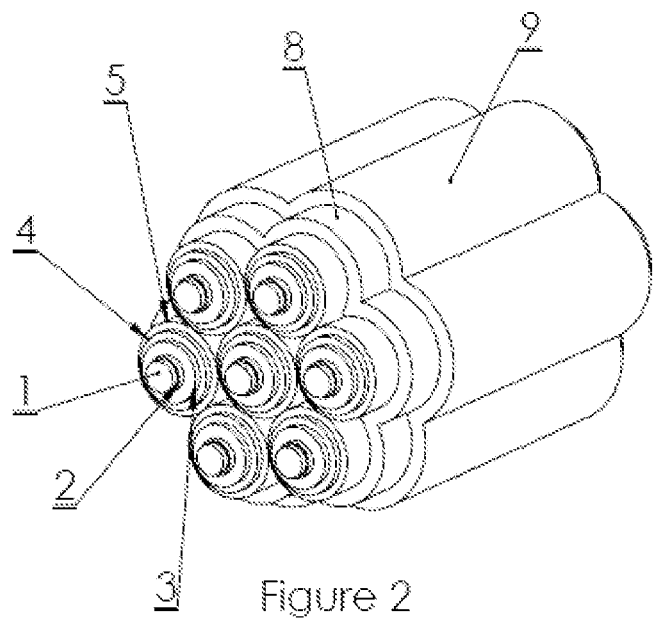
FIG. 2 is an isometric view of a first embodiment of multiple glass fibers encased in a single conductive coated shielding layer.

FIG. 2 shows multiple, single-conductive-coated-layer glass fibers 1 with electrically insulating layers 3, 5 under and over the first conductive coating 4. The multiple fibers are encased in a single shielding layer 8, with an additional outer electrically insulating layer 9. Shown are 7 coated glass fibers bundled into a cable. As in FIG. 1, each glass fiber may or may not have a coating layer 2 directly on the glass fiber 1, with an insulating layer 3 coated directly onto that.

The insulating material may be as described above, and it may be applied as described above. A conductive coating 4 is applied to the first insulation layer. A second insulation layer 5 is then applied to the conductive layer 4. The multiple fibers are bundled into a cable and then a shielding layer 8 is applied so it encases the cable. The shielding layer may be applied through a vapor deposition process and may be made of one or more conductive materials such as copper, silver, gold, or platinum. This layer is then coated with an insulation layer 9 which protects the conductive shielding below it. The insulation layer may be one of those listed above.

The shielding layer may be in contact with filters and may work with other techniques to limit EMI. For example, spread spectrum and frequency hopping techniques can be used in both digital and analog radio systems reduce or eliminate the unwanted interference. A simple resistor and capacitor in series may be included in the electrical circuit of the shielding layer to suppress EMI, especially in circuits carrying less than 2 amperes of current.

Integrated circuits can be a source of EMI if they are coupled to large objects such as heat sinks, circuit board planes, and cables. Decoupling capacitors across the power supply, series resistors for the rise time control of high-speed signals, voltage filtering, and shielding components such as conductive gaskets are ways of shielding the cable from EMI.

The level of radiation depends upon the height above the ground plane or power plane and the length of the conductor in relation to the wavelength of the signal component. At lower MHz frequencies, radiation in the form of common-mode noise is mostly through external cables. A braid-breaker or choke may be employed with the shielding layer to reduce the common-mode noise. At higher than MHz frequencies several techniques are used to reduce EMI. These techniques include wave shaping with series resistors, embedding traces in the integrated circuit between two planes, adding conductive gaskets, copper tape, or conductive coated cases.

Shielding and grounding can divert EMI away from the receiver by providing a low-impedance path. Shielding electrical housings and joints can reduce both emissions and reception of EMI by circuits contained in the housings. Electrical conductors in cables can be shielded within a surrounding conductive layer that is grounded at both ends. Grounding planes can be used for RFI. Decoupling or filters with RF chokes and/or RC at critical points (cable entry and near high speed switches) can be effective. Cables and wires can be made less susceptible to EMI though the use of transmission line techniques such as balanced differential signal and return paths, and impedance matching. Antenna structures like loops of circulating current and resonant mechanical structures should be avoided to reduce susceptibility to EMI. Other methods of making something less susceptible are to add fuses, transient absorbers, or design for operation at higher signal amplitudes, reducing the relative noise level in comparison.

Different materials act as better filters for different ranges of EMI frequency. Copper is commonly used for RFI because it absorbs radio and magnetic waves. Any gaps in the shielding must be significantly smaller than the radiation that is being kept out. Another method of canceling EMI reception is to use a method called twisted pair cabling, described in detail in the context of the present invention below.

Figure 3:
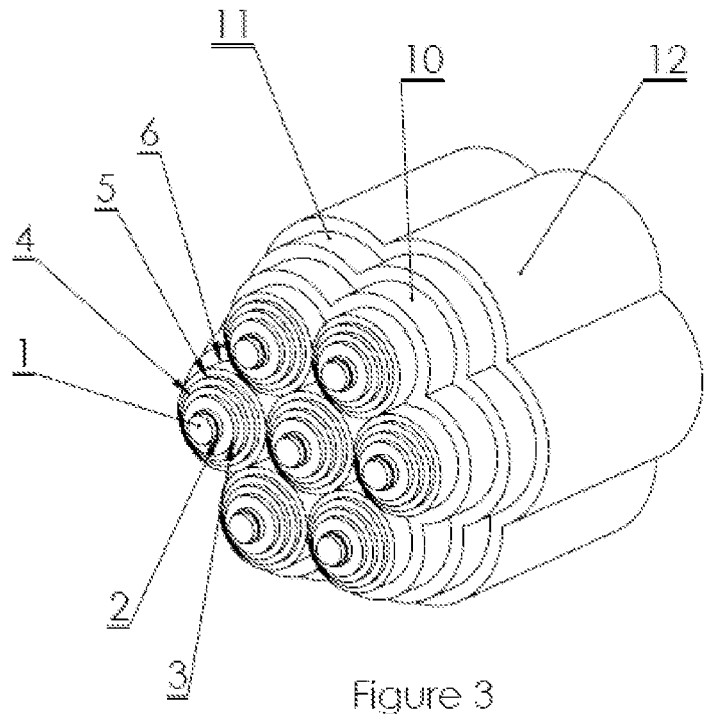
FIG. 3 is an isometric view of multiple, coaxial construction, multi-conductive-coated-layer glass fibers bundled together so that their outer shielding layers make electrical contact.

FIG. 3 shows multiple, single-conductive-coated-layer glass fibers 1 with electrically insulating layers 3, 5 under and over the first conductive coating 4. Shown are 7 coated glass fibers bundled into a cable, though other numbers are within the scope of the invention. The exact number of fibers is dependent on the application, and may be varied as needed. As in FIG. 1, each glass fiber may or may not have a coating layer 2 directly on the glass fiber 1, with an insulating layer 3 coated directly onto that.

The insulating material may be as described above, and it may be applied as described above. A conductive coating 4 is applied to the first insulation layer. A second insulative layer 5 is then applied to the conductive layer 4. A second conductive coating 6 may be applied to the second insulation layer. This second conductive coating 6 is a shielding layer 6. The multiple fibers are bundled into a cable.

The multiple fibers are bundled together so that their outer shielding layers 6 make electrical contact with each other.

Additional insulating and shielding layers can be added for additional protection against EMI. The shielding layer 6 is coated with a third insulative layer 10. For additional shielding, a third conductive layer 11 and fourth insulative layer 12 can be added. The ends of the shielding layer of the glass cored fiber are electrically attached to a fitting that is appropriately grounded, there-by grounding the entire shielding layer and shunting any EMI off to ground. Connector designs could accommodate EMI shielding within portions of the connector housing.

In another embodiment, special optical and electrical connectors that have optical signal connections, and electrical signal or energy connections are used on the ends of the glass fibers or cable of multiple fibers. In a further embodiment, special optical and electrical connectors also have a ground connection to a shielding layer in the coated glass fiber or cable of multiple coated glass fibers. In a further embodiment, the EMI transmission from the conductive surface employs the use electrical filtering or choke technology one or both fitting ends.

Figure 4:
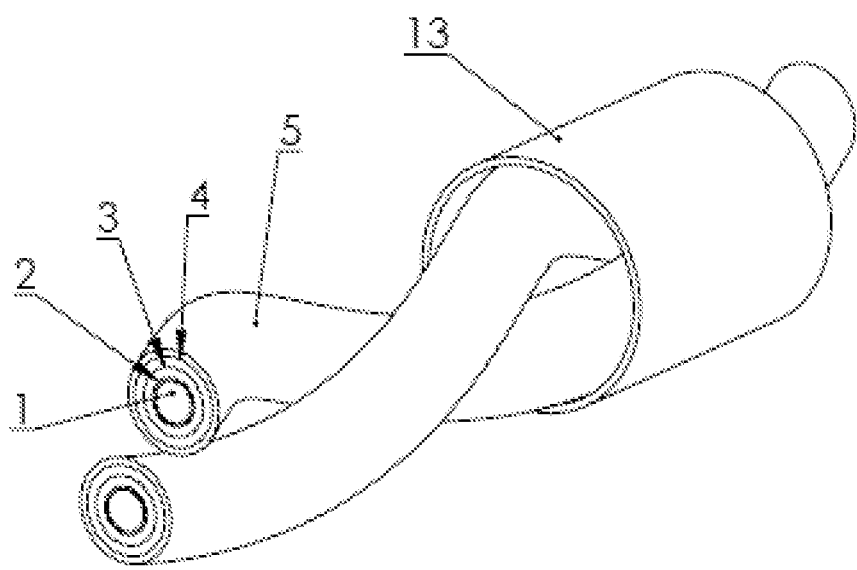
FIG. 4 is an isometric view of a twisted pair of glass cored fibers.

FIG. 4 shows the use twisted pairs of glass cored fibers with a minimum of one conductive layer and an electrically insulating layer above and below the conductive layer, in cables to reduce EMI susceptibility. Each coated fiber in the pair has a construction as described above with a center glass fiber core 1, with or without a graphite coating 2 on the fiber 1, an insulation layer 3, at least one conductive layer 4. Multiple conductive layers are envisioned, with additional insulation layers between any two conductive layers, and an external insulation layer as listed above. The two coated fibers 1 are twisted in a pair, and covered by an external insulation layer 13 to hold the pair together. Additional EMI protection could be accomplished with an additional shielding conductive layer between the twisted pair and the outer insulation.

Figure 5:
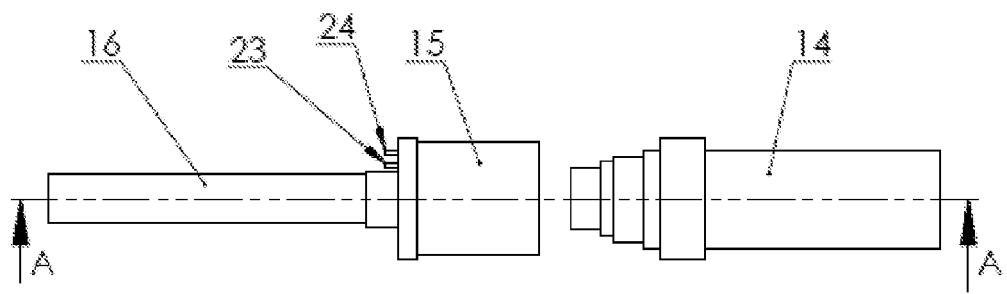
FIG. 5 shows a connector on one end of a coaxial, multi-conductive-coated-layer, glass cored fiber, in which there is an electrical connection and an optical connection to the fiber.
Figure 5A:
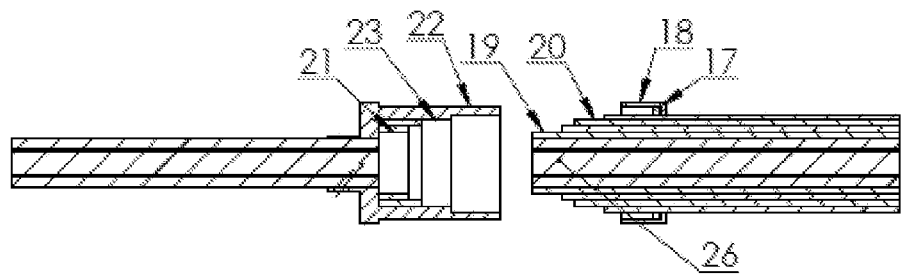
FIG. 5A is a longitudinal, cross sectional view of the connector of FIG. 5 taken along line A-A.

FIG. 5 and FIG. 5A show a connector on one end of a coaxial conductive coated glass cored fiber 14, in which there is an electrical connection to the electrically conductive layer of the fiber, there is an electrical connection to the shielding layer of the fiber, and there is an optical connection to the fiber. In FIG. 5, the right side shows a coaxial conductor coated glass core fiber 14. The left side of FIG. 5 shows a connector 15 (optionally mounted to an instrument box) with a glass core fiber 16 permanently attached and leaving the connector to the left. The coaxial conductor coated glass core fiber 14 has a stop 17 (See FIG. 5a) and a cap 18 for attaching the fiber to the connector 15 through a screw type mechanism that forces the two together and holds them in place (or other mechanism that accomplished the same purpose). The layers of the fiber are cut to expose the electrical conductors [conductive coating 19 and shielding layer 20]. The cuts are matched in dimensions to the receiving contacts in the connector 15.

In the connector 15, the signal contact 21 is insulated from the connector housing 22 and shield conductor contact 23. The shield contact 23 may or may not be insulated from the connector housing 22. Individual conductors from the signal contact 23 and the shield contact 24 extend out the back of the connector and are available for an electrical connection. The optical fiber 16 is bonded into the connector 15 so that there is a minimum gap between the optical fiber 16 and an optical fiber 26 of the coaxial conductor coated glass core fiber 14, when the fiber 14 and the connector 15 are attached.

FIGS. 5 and 5A show a minimum sized connection. Connections can be up-sized by attaching conductive rings to the outer conductive surfaces of the coaxial conductor coated glass core fiber 14 and scaling the connector appropriately.

FIGS. 5 and 5A show a single fiber connection, but this concept could be used with a bundle of fibers by having receptacles for each of the individual fibers of the bundle within the connector and the external shield layer similar to the fiber bundles shown in FIGS. 2 and 3, above.

FIGS. 5 and 5A show one method of contact to connect the signal conductors and the shield conductor, but spring contacts (lever arms, coiled spring, etc.) could also be used to assure electrical contact. In the same way, there are other methods beyond direct contact for making good optical contact (such as the use of gels, etc.).

Figure 6:
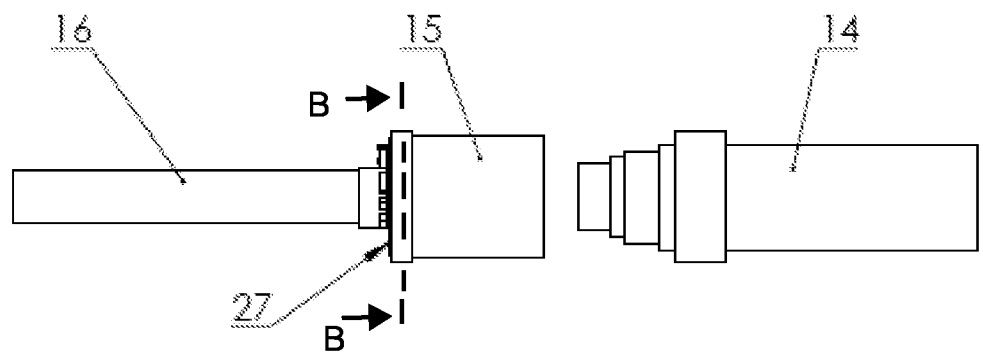
FIG. 6 shows a connector on a glass cored fiber in which there is an electrical connection by way of an electrical filter or choke, an electrical connection to the shielding layer of the fiber, and an optical connection to the fiber.
Figure 6A:
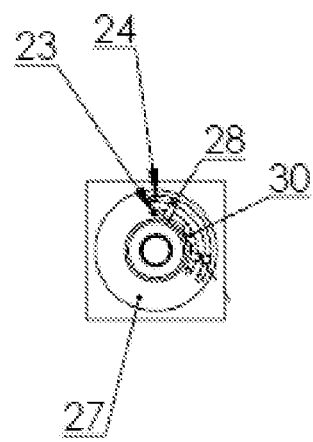
FIG. 6A is a cross sectional view of the connector of FIG. 6 taken along line B-B.

FIGS. 6 and 6A show a connector on one end of a coaxial conductor coated glass core fiber 14, in which there is an electrical connection by way of an electrical filter or choke 27, there is an electrical connection to the shielding layer of the fiber, and there is an optical connection to the fiber. FIG. 6 shows the filter circuit board 27 attached to the back of the connector 15 which is attached to fiber 16. With reference to FIG. 6A, the electrical signal travels from the signal conductor 23 to a capacitor 28 which is shunted across to a ground/shield circuit 24. An inductor 30 is in line with the signal and then the signal is again shunted to the ground/shield plane. The ground/shield and signal conductors can be attached to the board to carry the signal to its destination.

Figure 7:
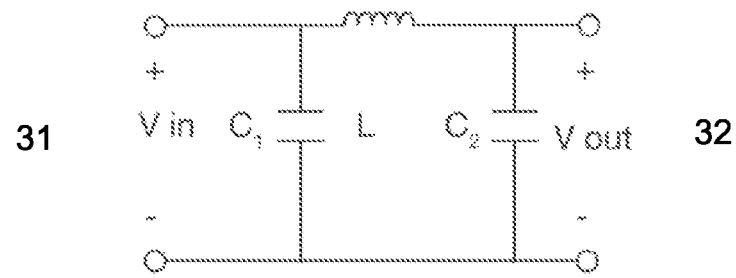
FIG. 7 is an electrical diagram of a filter or choke type electrical circuit for filtering out EMI for signals.

FIG. 7 shows an electrical filter or choke circuit with an input 31 and output 32. This is one of many typical designs that could be used to reduce the line noise caused by EMI. These circuits could be mounted on circuit boards 27 and attached to the connectors 15 as shown in FIG. 6 to reduce the line EMI prior to the signal passing on further.

Figure 8:
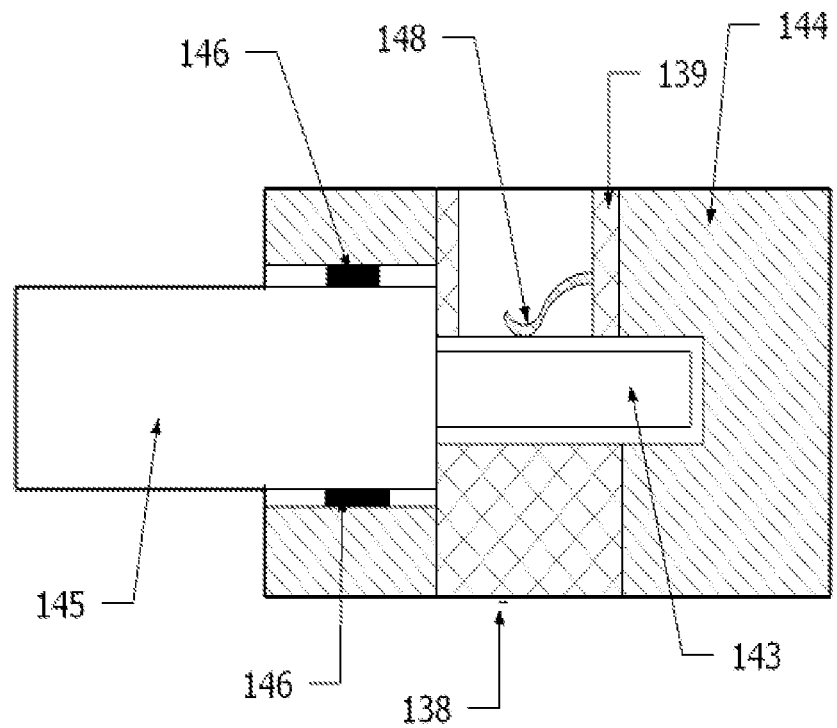
FIG. 8 is a diagrammatic view of a flat spring electrical connection to the conductive surface.

FIG. 8 shows a connector assembly 138 which incorporates a flat spring contact element 148. The fiber conductor body 145 is positioned in an internal chamber of the connector assembly 138. The flat spring contact element 148 makes contact with exposed conductive metal layer 143 of fiber conductor body 145. The flat spring contact element 148 applies a force on the conductive metal layer sufficient to ensure electrical contact without damaging the metal layer or underlying glass fiber. The connector assembly is constructed of an electrically insulating material 144 so the electrical current or signal flows in a controlled fashion from the fiber conductor 145 through the spring contact element 148, through a terminal connector 139 and out of the connector assembly conductor. In addition, connector assembly 138 could include multiple flat spring contact elements 148 to connect with conductive metal layer 143 for redundancy or other purposes.

The embodiment includes fluid seal(s) 146 to prevent fluids or humidity from entering the connector. FIG. 8 can also be scaled or modified according to the desired number of conductive metal layers. For example, connector assembly 138 could include multiple electrically isolated flat spring contact elements 148 to respectively connect with multiple conductive metal layers 143. Each conductive layer would have a portion exposed for contact with a flat spring contact element 148. Typically the outermost layer would be exposed farthest down the cable toward fiber conductor body 145, while the innermost layer would be exposed closest to the terminal end of the fiber, allowing for easy access by the respective contact elements 148.

Alternatively, a different radial portion could be removed so that each flat spring contact element 148 contacts fiber conductor body 145 at a different radial point. A first flat spring contact element 148 contacts the first conductive metal layer 143 of the fiber conductor body 145 at 12:00, while a second flat spring contact element 148 contacts a second conductive metal layer (not shown) or a second portion of the first conductive metal layer 143, which may or may not be electrically isolated from the first metal layer, at 6:00.

Figure 9:
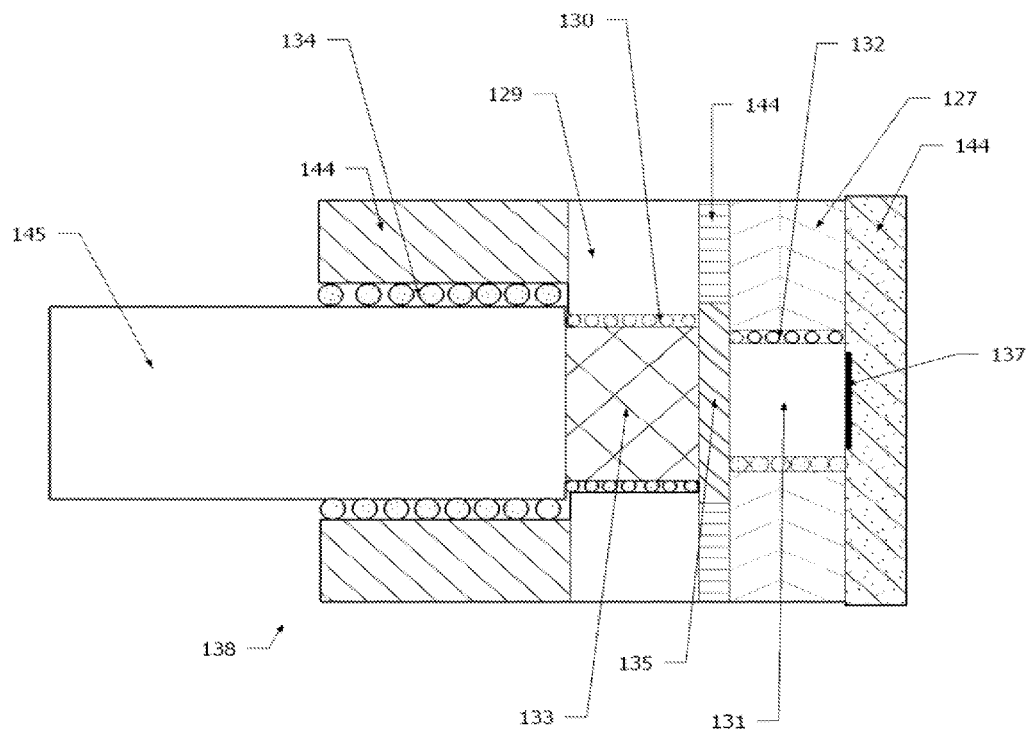
FIG. 9 is a diagrammatic view of a coaxial connection using coils, tubes (split or non-split), or mesh.

FIG. 9 shows a coaxial conductor connection using coils, tubes (split or non-split), mesh, or springs as the contact elements. The connector assembly 138 is made of an electrically insulating material 144. The fiber conductor body 145 is inserted into the internal chamber of the connector assembly. FIG. 9 shows a coaxial design with two exposed conductive metal layers 131, 133 in contact with two separate conductive spring coils 130, 132. The inner coil 132 makes electrical contact with the inner conductive metal layer 131 and the outer coil 130 with the outer conductive metal layer 133. Also shown are two terminal connectors 127, 129 to conduct the electrical signal from the coils and through the connector thus providing separate electrical pathways from the fiber conductor through the connector.

The contact element could be an electrically conductive adhesive. Likewise, the contact element can include an electrically conductive adhesive.

Insulation 135 is provided to prevent electrical signals from passing directly between the coils or between any electrically isolated metal layers. An additional coil 134 provides strain relief to the fiber conductor body 136 as it enters the connector assembly. Alternatively, additional coil 134 may contact a shielding layer, e.g., shielding layer 8, above, to ground any EMI present in body 145.

The coils or springs are canted or non-canted and are designed to be compressible against the metal layer of the fiber conductor. The coiled spring could extend 360 degrees around the connector assembly chamber or some portion thereof. The figure shows two conductive pathways but the concept could be expanded to accommodate additional conductive pathways between the fine wire conductor and the connector. In addition, the glass fiber core can transmit optical energy or signals. The connector assembly provides an optical connector 137 for transmission of the optical signals or energy, details not shown.

Figure 10:
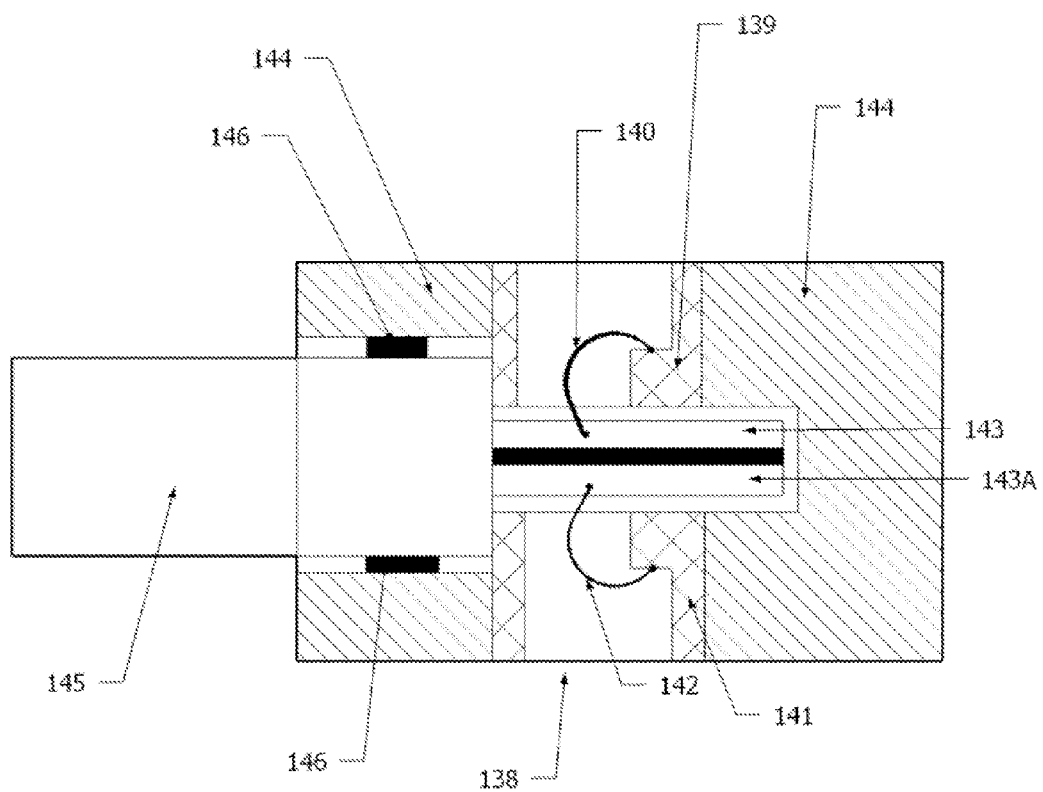
FIG. 10 is a diagrammatic view of one or more electrical connections from a metalized surface on a glass fiber to individual connector assembly (or electrodes) using wire or ribbon ball bonding from one surface to the other.

FIG. 10 shows a connector for use with a cable 145 that includes a split conductive metal layer. The metal layer can be split into two or more discrete and independent conductive pathways on the same metal layer, 143 and 143A. This can be done by patterning the metal layer during metal deposition, laser patterning of the metal or other techniques. The connector assembly 138 is made from a nonconductive, electrically insulting material 144. The drawings show a nonconductive connector assembly. However the actual assembly could be conductive as long as it allows for controlled signal transmissions per design requirements. For example, there could be a nonconductive layer between the assembly and the conductive pathway(s) on the fiber. The fiber conductor body 145 is inserted into the connector assembly 138 where the first contact element 140 comes in contact with a first portion of the split metal layer 143 and the electrical current or signal passes through the first terminal connector 139 and to the next conductor (not shown). The electrical connections from a metalized surface on a glass fiber to individual connector assembly (or electrodes) can be made using wire or ribbon ball bonding from one surface to the other.

The second contact element 142 comes in contact with the second portion of the split metal layer 143a and the electrical current or signal passes through the second terminal connector 141 and to the next conductor (not shown). A fluid seal 146 prevents fluids or humidity from entering the connector. The connector assembly can include an optical connector (not shown) for transmitting optical signals or energy.

The contact elements 140, 142 could be coils, tubes, wires, bands, rings, ball, conductive adhesive or other conductive connections that can make reliable electrical contact with the metal layer of the conductor body without damaging the metal layer or underlying glass fiber. They could utilize a contact adhesive for improving the connections, including an electrically conductive contact adhesive. Two connector pathways are shown but the number could be expanded circumferentially around the connector's internal chamber or longitudinally along the chamber. The connector assembly and the conductor body may also include a keying mechanism to ensure that the appropriate contact element lines up with the desired metal pathway.

Figure 11:
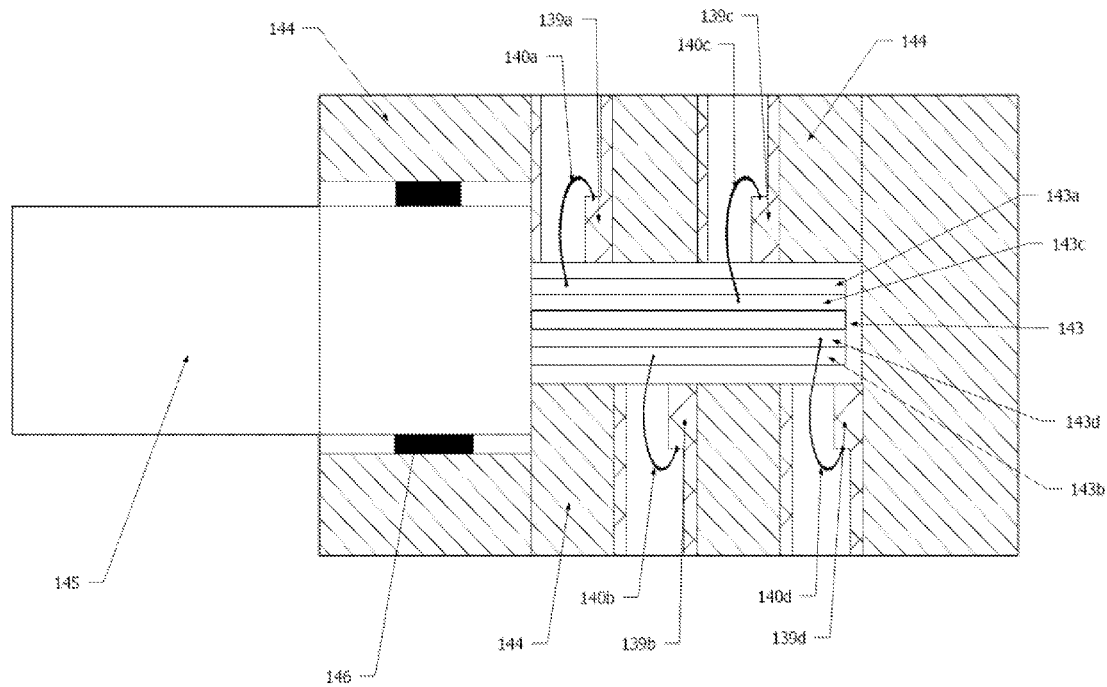
FIG. 11 is a diagrammatic view of a single conductive surface split into five conductive surfaces and a seal at the fiber entrance to the connection.

FIG. 11 is similar to FIG. 10 except the connector assembly 138 includes additional connector pathways along the length of the connector's internal chamber. The fiber conductor 145 has the metal layer split into multiple discrete and independent conductive pathways 143. The exact number will depend on the application, and may vary. As shown in FIG. 11, the first contact element 140a comes in contact with a first conductive metal pathway 143a on the split metal layer 143 and the electrical current or signal passes through the first terminal connector 139a and to the next conductor (not shown). Additional contact elements 140 b, c, d, . . . make contact with the other conductive pathways 143 b, c, d, . . . on the split metal layer 143 and the electrical current or signal passes through separate terminal connectors 139 b, c, d . . . and to other conductors (not shown). The insulation material 144 provides electrical isolation of the various connector pathways. A fluid seal 146 prevents fluids or humidity from entering the connector. The connector assembly can include an optical connector (not shown) for transmitting optical signals or energy.

Figure 12:
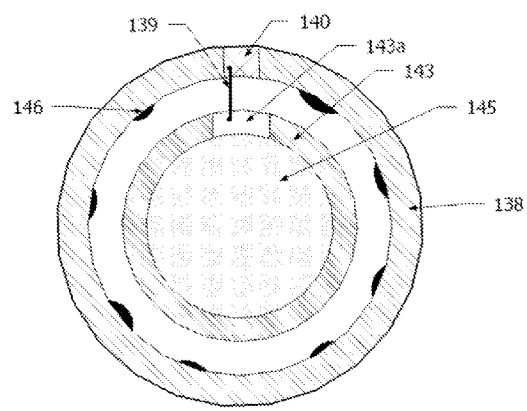
FIG. 12 is a cross sectional view showing a connection to the conductive surface more clearly.

FIG. 12 shows a cross-section of one embodiment of a fiber conductor body 145 inserted in a connector assembly 138 with one pathway shown. A contact element 140 comes in contact with one pathway 143a on the split metal layer 143 and the electrical current or signal passes through the first terminal connector 139 and to the next conductor (not shown). The connector assembly can include an optical connector (not shown) for transmitting optical signals or energy. Seal member 146 prevents the inflow of fluids or humidity. In the cross section shown only one contact element visibly contacts one pathway (within that linear cross section). The other contact elements would contact their respective pathways either proximally or distally of the cross section shown. In an alternative embodiment, each contact element may be at the same linear location, but be radially offset.

Figure 13:
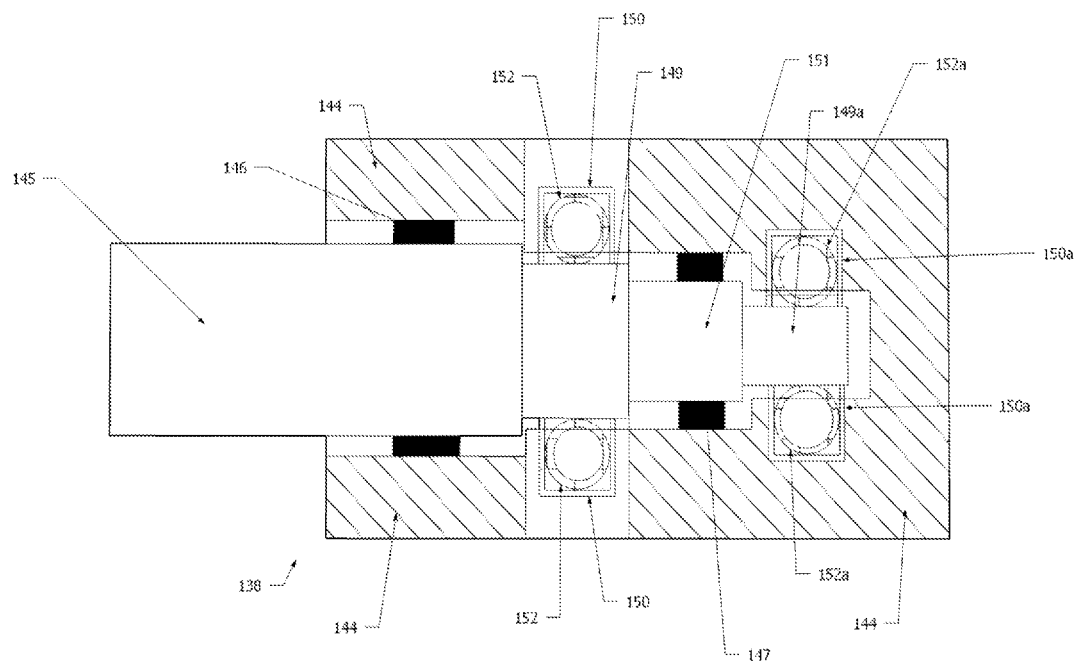
FIG. 13 is a diagrammatic view of a multi-layer (coaxial) fiber with each layer electrically connected to a connector ring/electrode using a canted/non-canted circular coiled spring inside the connector ring.

FIG. 13 shows a multi-layer (coaxial) fiber conductor body 145 with a first conductive metal layer 149 and a second conductive metal layer 149a making electrical contact with a first contact element 152 and a second contact element 152a, respectively. Contact elements 152 and 152a are in the form of a circular coiled spring inside a terminal connector assembly 150 and 150a. The circular coiled spring can make contact 360 degrees around the conductive metal layer's 149, 149a surface. The terminal connector assembly 150 is connected to another conductor for continued electrical transmission.

The contact element 152 and terminal connector assembly 150 can be discrete units located at one or more locations around the circumference of the of the connector's assembly internal chamber. In this configuration, the contact element 152 is a ring or other compressible shape or material. The connector assembly is made from an electrically insulating material 144 to prevent unwanted electrical contact between the separate electrical pathways. There are seals 146, 147 between the coaxial conductors and at the entrance of the connector assembly 150. Both seals 146, 147 are intended to prevent fluid ingress and electrical conductivity. This configuration could be used with one or more conductive metal layers on the fine wine conductor, as shown with an insulting material 151 between the metal layers 149, 149a.

Figure 14:
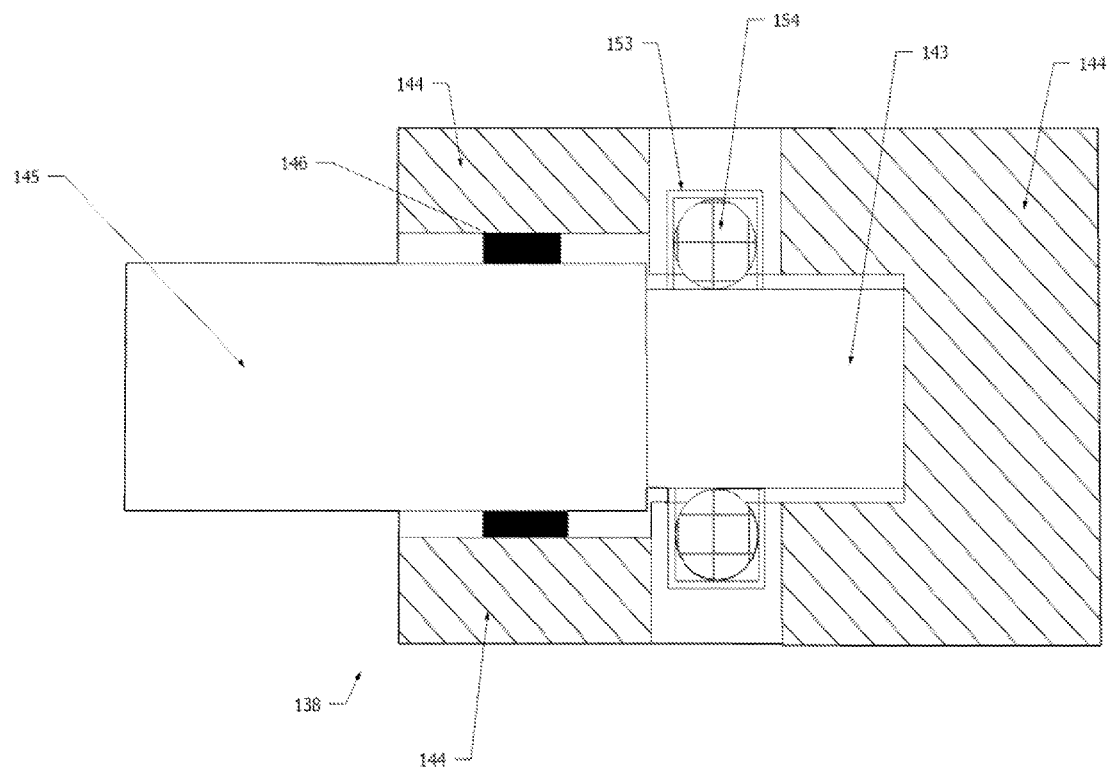
FIG. 14 is a diagrammatic view of a multi-layer (coaxial) fiber with each layer electrically connected to a connector ring/electrode with a conductive elastomer O-ring.

FIG. 14 is similar to FIG. 13 except it uses a conductive elastomer O-ring 154 to make the electrical connection between the surface of the conductive metal layer surface 143 on the conductor fiber body 145 and the terminal connector assembly 153. This would work for one or more conductive layers on the fiber. A fluid seal 146 prevents fluids or humidity from entering the connector. The connector assembly can include an optical connector (not shown) for transmitting optical signals or energy.

Figure 15:
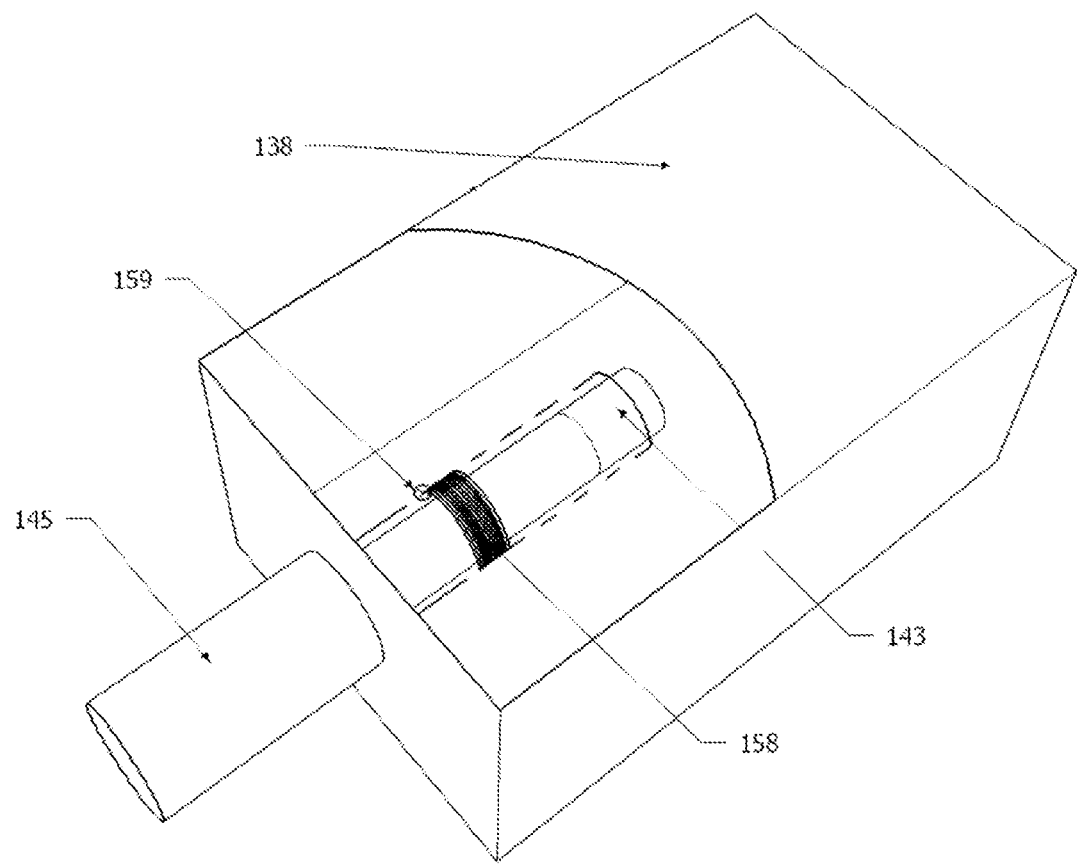
FIG. 15 is an isometric view of a connector using a strap to hold the fiber into a connector assembly.

FIG. 15 shows the use of a strap 158 to hold the fiber conductor body 145 into the connector assembly 138. The strap is tightened by rotating a screw mechanism 159. The connector assembly 138 includes a conductive sleeve into which the fiber core with its exposed conductive metal layer 143 is inserted. The contact between the connector assembly's conductive sleeve and the fiber conductor's metal layer provides a precise fit to ensure electrical contact without damaging either surface. The conductive sleeve is connected to a terminal connector (not shown) to permit electrical transmission. The connector assembly can include an optical connector (not shown) for transmitting optical signals or energy.

Figure 16:
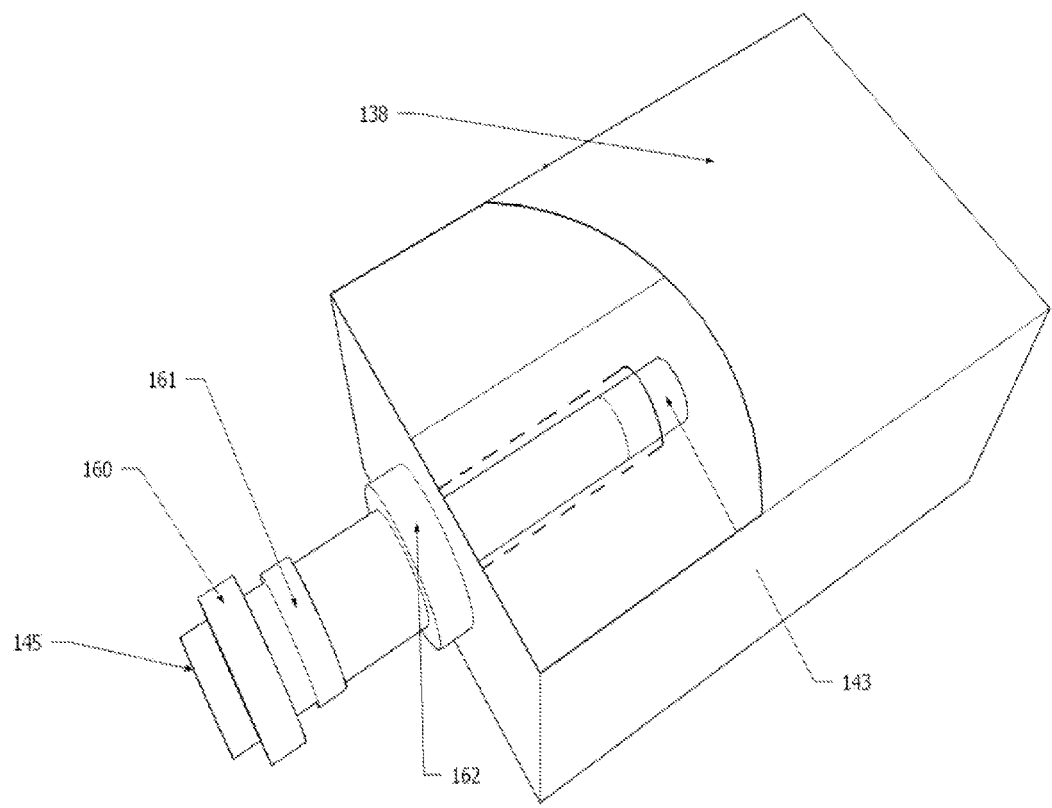
FIG. 16 is an isometric view of a connector holding a fiber in a connector assembly using a feature fixed to the fiber and that is held against the assembly by a movable cap that attaches to the assembly by a thread or other type of retaining feature.

FIG. 16 shows a fiber conductor body 145 being held in a connector assembly 138 using an anchoring feature 161 fixed to the fiber conductor body 145 and held against the connector assembly 138 by a movable cap 160 that attaches to the connector assembly by a threaded or other type of retaining feature 162. The connector assembly 138 includes a conductive sleeve into which the fiber core with its exposed conductive metal layer 143 is inserted. The contact between the connector assembly's conductive sleeve and the fiber conductor's metal layer provides a precise fit to ensure electrical contact without damaging either surface. The conductive sleeve is connected to a terminal connector (not shown) to permit electrical transmission. The connector assembly can include an optical connector (not shown) for transmitting optical signals or energy.

Figure 17:
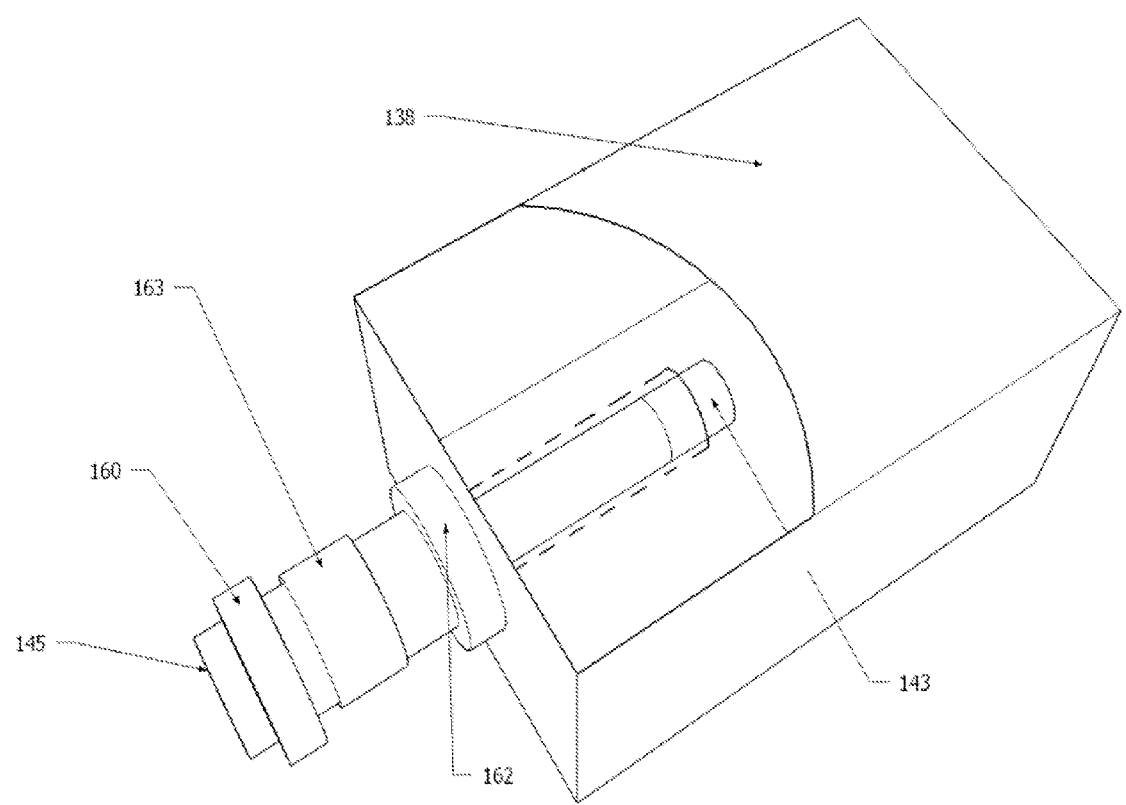
FIG. 17 is an isometric view of a connector with a movable, compressible, item on the fiber, that is placed in position, and then compressed against the connector assembly by the movable cap that attaches to the assembly.

FIG. 17 is similar to FIG. 16, but shows a movable, compressible, ring 163 on the conductor fiber body 145. Ring 163 is placed in position and then compressed against the connector assembly 138 by the movable cap 160 that attaches to the assembly by a threaded or other type of retaining feature 162. The compressed material pushes against the fiber, holding it in place in the connector assembly. The connector assembly 138 includes a conductive sleeve into which the fiber core with its exposed conductive metal layer 143 is inserted. The contact between the connector assembly's conductive sleeve and the fiber conductor's metal layer provides a precise fit to ensure electrical contact without damaging either surface.

Figure 18:
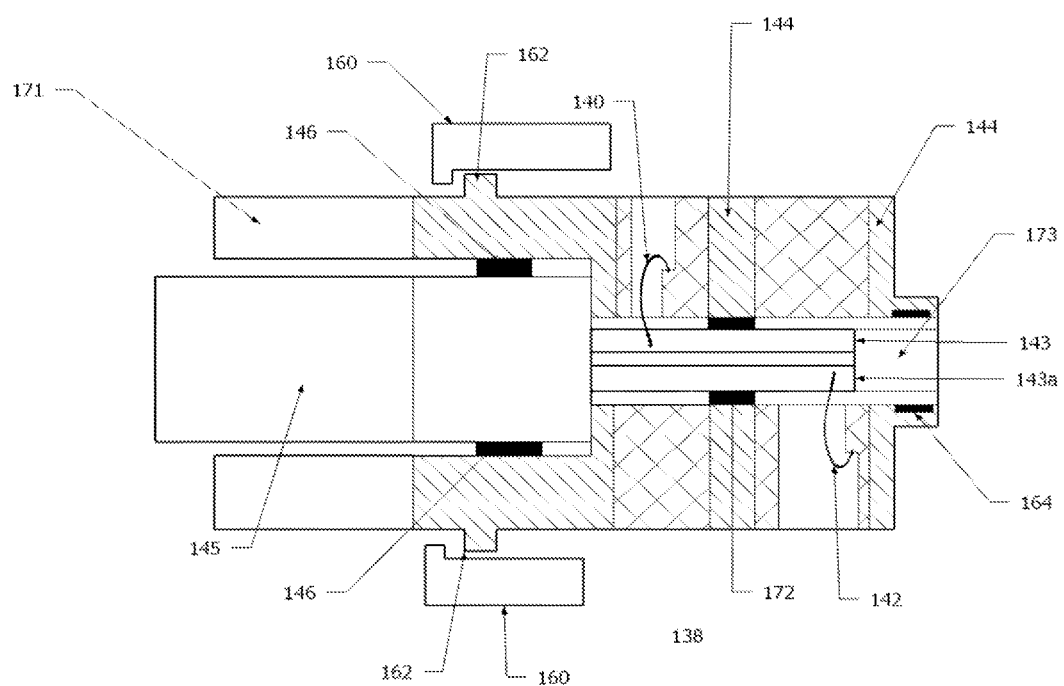
FIG. 18 is a diagrammatic view of another connector embodiment.

FIG. 18 shows a combination of some of the ideas disclosed. It shows a conductive fiber body 145 positioned within a connector assembly 138. It shows multiple conductive metal pathways 143, 143a on a single metalized fiber surface. The connector assembly 138 is made from a nonconductive, electrically insulating material 144. The contact elements 140, 142 come in contact with respective portions of the split metal layer 143, 143*a* and the electrical current or signal passes through the terminal connectors and to another conductor (not shown). A fluid seal 146 prevents fluids or humidity from entering the connector and seals 172 electrically isolate the different electrical pathways. A polymer material 171 provides strain relief as the conductive fiber body 145 enters the connector assembly 138. The end of the optical glass fiber 173 is secured to the connector assembly with an adhesive 164, which may be a permanent adhesive. The fiber body is held in the connector assembly with a cap 160 and retaining feature 162. It is intended that this figure shows only one example of many different combinations possible using the techniques disclosed.

Figure 19:
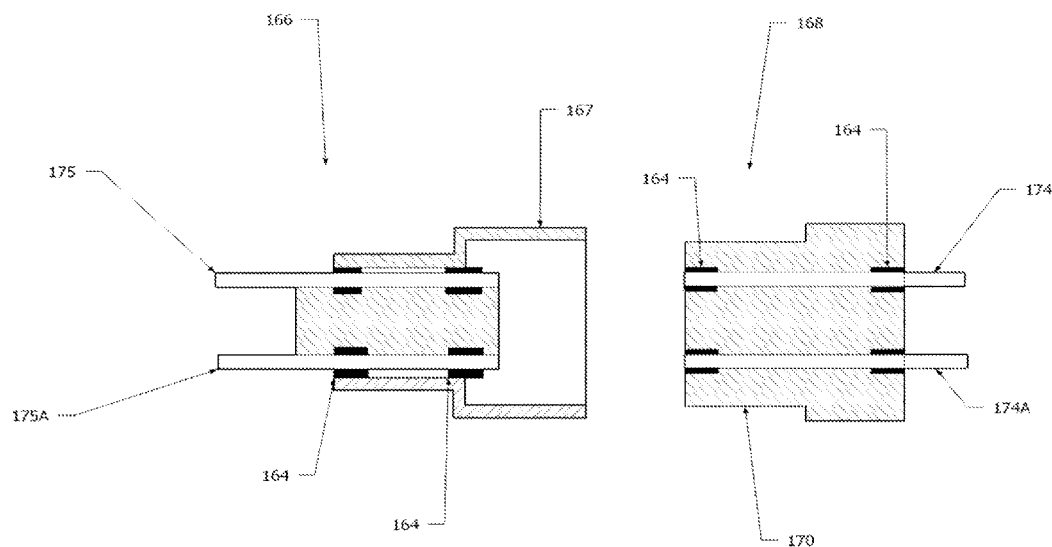
FIG. 19 is a diagrammatic view of two optical fibers with connectors that are not yet connected.
Figure 19A:
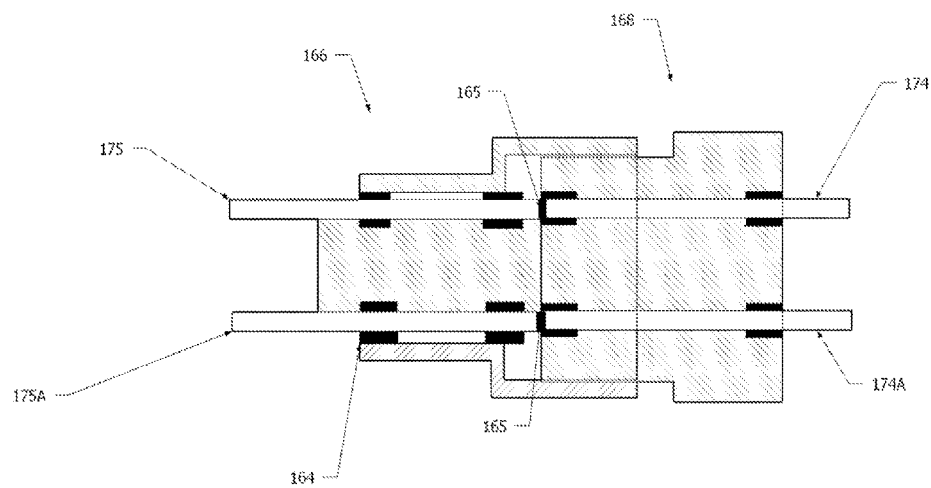
FIG. 19a is a diagrammatic view of the connectors of FIG. 19 after they are connected.

FIG. 19 shows two optical fibers 174, 174*a* being connected to two other optical fibers 175, 175*a* using a two part optical connector assembly 166, 168. Adhesives 164 are used to secure the fiber to the connector assembly. The two parts of the connector assembly are connected using a threaded cap 167 which connects to retaining feature 170 or other retaining method. As shown in FIG. 19*a*, the optical fibers are fused with an adhesive 165, such as an optical adhesive, or other means. The connectors could incorporate the various electrical connectors as described above to connect the electrical portions of the fibers 174, 174*a*, 175, 175*a* as desired.

What is claimed is:
1. An apparatus, comprising:
   a fine wire conductor with an outer diameter no greater than about 750 microns, including:
   a fiber core comprising silica or glass,
   a first insulative layer on the fiber core,
   a coaxial first conductive coating on the first insulative layer configured and arranged to carry electrical signals along the length of the conductor,
      wherein the first conductive coating comprises a first electrically isolated pathway and a second electrically isolated pathway,
   a second insulative layer on the first conductive coating,
   a shielding layer outside the second insulative layer, and
   an outer insulating layer.

2. The apparatus defined in claim 1, further comprising a coating layer between the fiber core and the first insulative layer.

3. The apparatus of claim 2, wherein the coating layer is a graphite layer.

4. The apparatus of claim 2, further comprising a second conductive coating on the second insulative layer and a third insulative layer on the second conductive coating.

5. The apparatus defined in claim 2, wherein the coating layer or the first insulative layer hermetically seals the fiber core.

6. The apparatus of claim 1, further comprising a connector, the connector including
   a connector shielding layer adapted to connect to the shielding layer,
   a ground connection connected to the connector shielding layer to ground the connector shielding layer to a ground.

7. The apparatus of claim 6, wherein the connector shielding layer further comprises a choke filter.

8. The apparatus of claim 6, wherein connector further comprises a first connector conductive layer, and wherein the first conductive coating is electrically connected to the first connector conductive layer.

9. The apparatus of claim 8, wherein the connector further comprises an optical mechanism, and wherein the fiber core is optically linked to the optical mechanism in the connector.

10. The apparatus of claim 6 wherein the connector comprises a contact adhesive, and wherein the fine wire conductor is connected to the connector via the =contact adhesive.

11. The apparatus of claim 6, wherein the connector further comprises a retaining mechanism.

12. The apparatus defined in claim 1, wherein the fine wire conductor has an outer diameter no greater than about 300 microns.

13. The apparatus defined in claim 1, wherein the drawn fiber core includes a cladding comprised of glass or silica.

14. The apparatus defined in claim 1, wherein the first conductive coating is selected from the group consisting of aluminum, silver, gold, copper or platinum.

15. The apparatus defined in claim 14, wherein the first conductive coating is between 200 nm thick and 40 microns thick.

\* \* \* \* \*